(12) United States Patent
Martinez (10) Patent No.: US 9,060,779 B2
(45) Date of Patent: Jun. 23, 2015

(54) CLIP DEVICES AND METHODS OF DELIVERY AND DEPLOYMENT

(75) Inventor: Michelle D. Martinez, Winston-Salem, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 806 days.

(21) Appl. No.: 13/197,497

(22) Filed: Aug. 3, 2011

(65) Prior Publication Data

US 2012/0041455 A1 Feb. 16, 2012

Related U.S. Application Data

(60) Provisional application No. 61/372,283, filed on Aug. 10, 2010.

(51) Int. Cl.
| | | |
|---|---|---|
| *A61B 17/10* | (2006.01) | |
| *A61B 17/128* | (2006.01) | |
| *A61B 17/122* | (2006.01) | |

(52) U.S. Cl.
CPC ......... *A61B 17/1285* (2013.01); *A61B 17/1227* (2013.01)

(58) Field of Classification Search
CPC ........... A61B 17/0487; A61B 17/1285; A61B 17/122; A61B 2017/1227; A61B 17/128
USPC .......................... 606/139, 142, 143, 151, 157
See application file for complete search history.

(56) References Cited

U.S. PATENT DOCUMENTS

| 5,445,167 A | 8/1995 | Yoon et al. | |
|---|---|---|---|
| 2008/0312665 A1* | 12/2008 | Shibata et al. | 606/142 |
| 2010/0044251 A1* | 2/2010 | Itoh et al. | 206/63.3 |
| 2010/0160935 A1* | 6/2010 | Karpiel et al. | 606/142 |

FOREIGN PATENT DOCUMENTS

| JP | 2010-46258 | 3/2010 |
|---|---|---|
| WO | WO2010/080386 | 7/2010 |

OTHER PUBLICATIONS

International Search Report and Written Opinion for PCT/US2011/046425 mailed Jan. 13, 2012, 14 pgs.
International Preliminary Report on Patentability for PCT/US2011/046425 completed Feb. 12, 2013, 9 pgs.
(Continued)

*Primary Examiner* — Gregory Anderson
(74) *Attorney, Agent, or Firm* — Brinks Gilson & Lione (57) ABSTRACT

The present embodiments provide systems and methods for deploying at least one clip device. In a first embodiment, the system comprises a first clip device having first and second arms. The first clip device and an associated sliding ring are configured to be selectively advanced through a lumen of an inner catheter. Selective positioning of an outer catheter over a distal region of the inner catheter causes a distal region of the inner catheter to bow radially inward to form a constriction that securely engages the sliding ring of the first clip device, thereby allowing for partial closure and repositioning of the first clip device. In an alternative embodiment, a delivery system includes a single catheter having a tapered distal region, such that upon ejection of the sliding ring from the distal end of the catheter, the sliding ring is dimensioned to abut the distal end of the catheter. In any of the embodiments, multiple clips may be sequentially loaded and deployed using the delivery systems. Various clip designs and a loading cylinder are also disclosed.

20 Claims, 6 Drawing Sheets

(56) References Cited

OTHER PUBLICATIONS

Office Action for Japanese Patent Application No. 2013-524107 dated Feb. 18, 2014, 7 pgs., including English translation.
Requisition by Examiner for Canadian Patent Application No. 2807385 dated Jan. 13, 2014, 3 pgs.
Patent Examination Report No. 1 for Australian Patent Application No. 2011289675 dated May 31, 2013, 3 pgs.
Response to Patent Examination Report No. 1 for Australian Patent Application No. 2011289675 dated Apr. 9, 2014, 15 pgs.
Patent Examination Report No. 2 for Australian Patent Application No. 2011289675 dated May 14, 2014, 3 pgs.
Communication under Rule 161(1) and 162 EPC for European Patent Application No. 11743739.2 dated Mar. 19, 2013, 2 pgs.
Response to Communication under Rule 161(1) and 162 EPC for European Patent Application No. 11743739.2 dated Sep. 17, 2013, 10 pgs.
Examiners Report for Canadian Patent Application No. 2,807,385 dated Oct. 10, 2014, 2 pgs.
Response to Examination Report No. 2 for Australian Patent Application No. 2011289675 filed Jul. 8, 2014, 13 pgs.
Examination Report No. 3 for Australian Patent Application No. 2011289675 dated Sep. 3, 2014, 3 pgs.
First Office Action for Chinese Patent Application No. 201180039005.X dated Dec. 3, 2014, 17 pgs. including English translation.
Amended Claims for Japanese Patent Application No. 2013-524107 filed Jun. 18, 2014, 2 pgs.
Certified Decision for Patent for Japanese Patent Application No. 2013-524107 dated Nov. 4, 2014, 4 pgs.

* cited by examiner

CLIP DEVICES AND METHODS OF DELIVERY AND DEPLOYMENT

PRIORITY CLAIM

This invention claims the benefit of priority of U.S. Provisional Application Ser. No. 61/372,283, entitled "Clip Devices and Methods of Delivery and Deployment," filed Aug. 10, 2010, the disclosure of which is hereby incorporated by reference in its entirety.

BACKGROUND

Conventionally, a clip may be introduced into a body cavity through an endoscope to grasp living tissue of a body cavity for hemostasis, marking, and/or ligating. In addition, clips are now being used in a number of applications related to gastrointestinal bleeding such as peptic ulcers, Mallory-Weiss tears, Dieulafoy's lesions, angiomas, post-papillotomy bleeding, and small varices with active bleeding.

Gastrointestinal bleeding is a somewhat common and serious condition that is often fatal if left untreated. This problem has prompted the development of a number of endoscopic therapeutic approaches to achieve hemostasis such as the injection of sclerosing agents and contact thermo-coagulation techniques. Although such approaches are often effective, bleeding continues for many patients and corrective surgery therefore becomes necessary. Because surgery is an invasive technique that is associated with a high morbidity rate and many other undesirable side effects, there exists a need for highly effective, less invasive procedures.

Mechanical hemostatic devices have been used in various parts of the body, including gastrointestinal applications. Such devices are typically in the form of clamps, clips, staples and sutures, which are able to apply sufficient constrictive forces to blood vessels so as to limit or interrupt blood flow. One of the problems associated with conventional hemostatic devices, however, is that many devices are not strong enough to cause permanent hemostasis. Further, typically once such mechanical hemostatic devices are at least partially deployed, they cannot be opened and closed repeatedly before the final release of the device, which may result in possible permanent deployment of the device at an undesirable location.

Still further, mechanical hemostatic devices typically are loaded, one at a time, within an introducer equipped to deliver and deploy the device. A first hemostatic device may be deployed, but if it becomes desirable to deliver and deploy a second hemostatic device, the introducer typically must be removed from the patient's body in order to load the second hemostatic device. The introducer then is loaded back into the patient's body to deploy the second hemostatic device, and the process is repeated for each subsequent device. However, the process of deploying only one hemostatic device at a time may become very time consuming and inconvenient, causing significant delays when it may be imperative to quickly stop bleeding.

SUMMARY

The present embodiments provide systems and methods for deploying at least one clip device. In each embodiment, multiple clips may be sequentially loaded and deployed using the delivery systems. Various clip designs and a loading cylinder are also disclosed.

In a first embodiment, the system comprises a first clip device having first and second arms. The first clip device and an associated sliding ring are configured to be selectively advanced through a lumen of an inner catheter. Selective positioning of an outer catheter over a distal region of the inner catheter causes a distal region of the inner catheter to bow radially inward to form a constriction that securely engages the sliding ring of the first clip device. When the sliding ring is securely engaged, the first and second arms of the first clip device are movable longitudinally relative to the sliding ring, thereby allowing for partial closure and repositioning of the first clip device.

Advantageously, in this manner, any number of clip devices may be sequentially loaded into the lumen of the catheter and deployed, one at a time, without the need to remove the inner and outer catheters from the patient's body and individually re-load clip devices, thereby reducing operating time. Further, each of the clip devices advantageously may move between the open and closed states any number of times before final deployment.

In an alternative embodiment, a delivery system includes a catheter having proximal and distal ends, a lumen extending therebetween, and a tapered distal region. The catheter comprises a first inner diameter at a location proximal to the tapered distal region, and further has a second inner diameter at the distal end, wherein the second inner diameter is less than the first inner diameter. The sliding ring comprises an outer diameter that is less than the first inner diameter of the catheter and greater than the second inner diameter of the catheter. The tapered distal region of the catheter is flexible such that application of a predetermined distally-oriented forced imposed upon the sliding ring ejects the sliding ring from the distal end of the catheter. Upon ejection of the sliding ring from the distal end of the catheter, the sliding ring is dimensioned to abut the distal end of the catheter. At this time, proximal retraction of the first and second arms of the first clip device relative to the sliding ring moves the clip device between the open and closed states.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Referring now to FIGS. 1-6, a first embodiment of a clip device is shown, along with an exemplary system for delivery and deployment of at least one of the clip devices. In this embodiment, first and second clip devices 20a and 20b are provided. The first clip device 20a comprises a first arm 30a and a second arm 40a. The first arm 30a has a proximal end 32a and a distal end 34a, while the second arm 40a has a proximal end 42a and a distal end 44a. The proximal end 32a of the first arm 30a and the proximal end 42a of the second arm 40a are joined together by a proximal securement member 60a, which may comprise an adhesive, solder, weld, mechanical attachment device, or any other suitable mechanism, that joins the proximal ends 32a and 42a of the arms 30a and 40a together.

The clip device 20a further comprises a sliding ring 50a, which has an inner diameter that is slightly larger than an outer diameter of the first and second arms 30a and 40a combined. The proximal securement member 60a limits proximal movement of the sliding ring 50a. In use, the sliding ring 50a is dimensioned to slide over the first and second arms 30a and 40a, causing the arms to move to a closed position, as explained further in FIG. 4 below.

Figure 1:
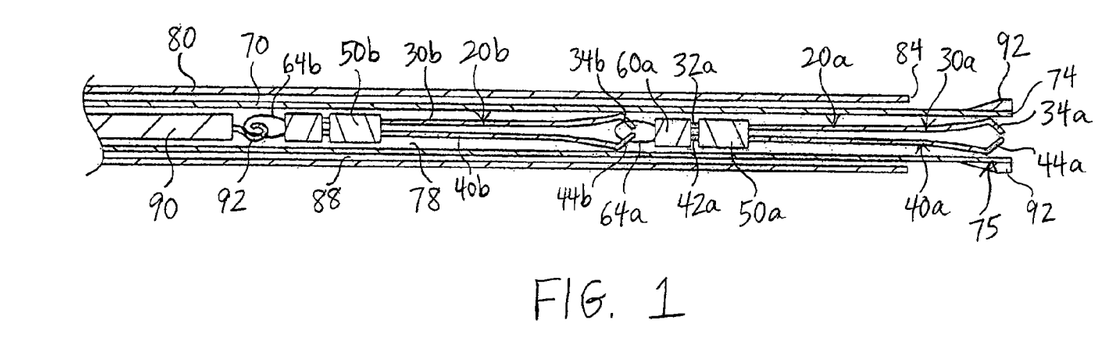
FIGS. 1-5 are side-sectional views illustrating an exemplary delivery system and sequence of deployment for at least one clip device.
Figure 2:
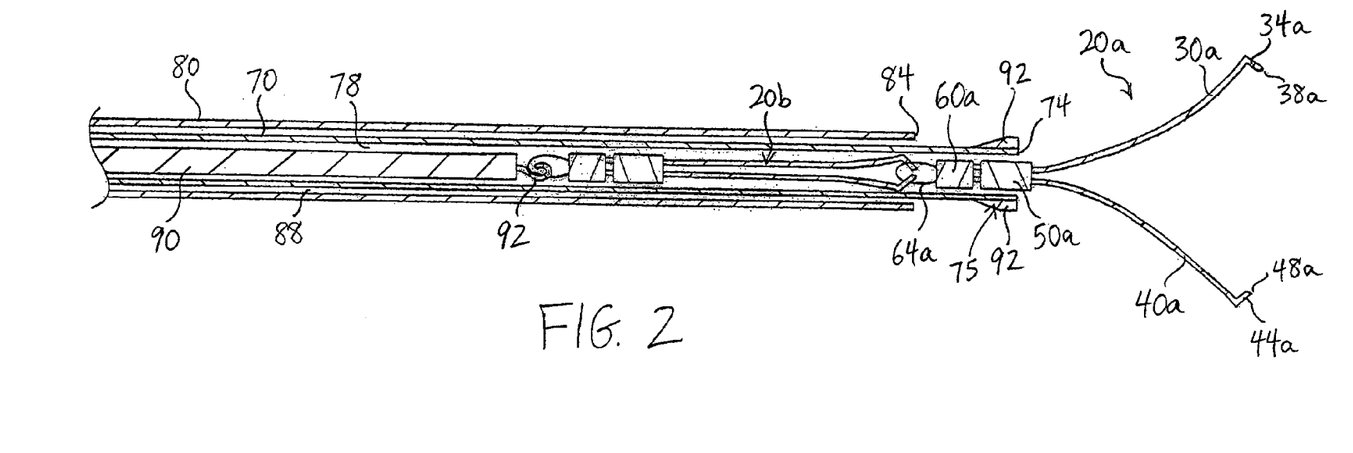

The distal ends 34a and 44a of the arms 30a and 40a are preferably bent in radially inward directions to form tips 38a and 48a, respectively, as best seen in FIG. 2. The tips 38a and 48a are configured to grasp and/or pierce tissue. While two arms 30a and 40a are depicted in the embodiment of FIGS. 1-5, it is contemplated that a greater number of arms may be used. For example, as explained in FIGS. 13-14 below, alternative clip devices 120a' and 120a" comprise three and four arms, respectively.

The first clip device 20a has a delivery state, an open state, and a closed state. In the delivery state, the first clip device 20a is disposed within a lumen 78 of an inner catheter 70. The lumen 78 of the inner catheter 70 is dimensioned such that the distal ends 34a and 44a of the arms 30a and 40a are held adjacent to one another in the delivery state, as depicted in FIG. 1.

Figure 3:
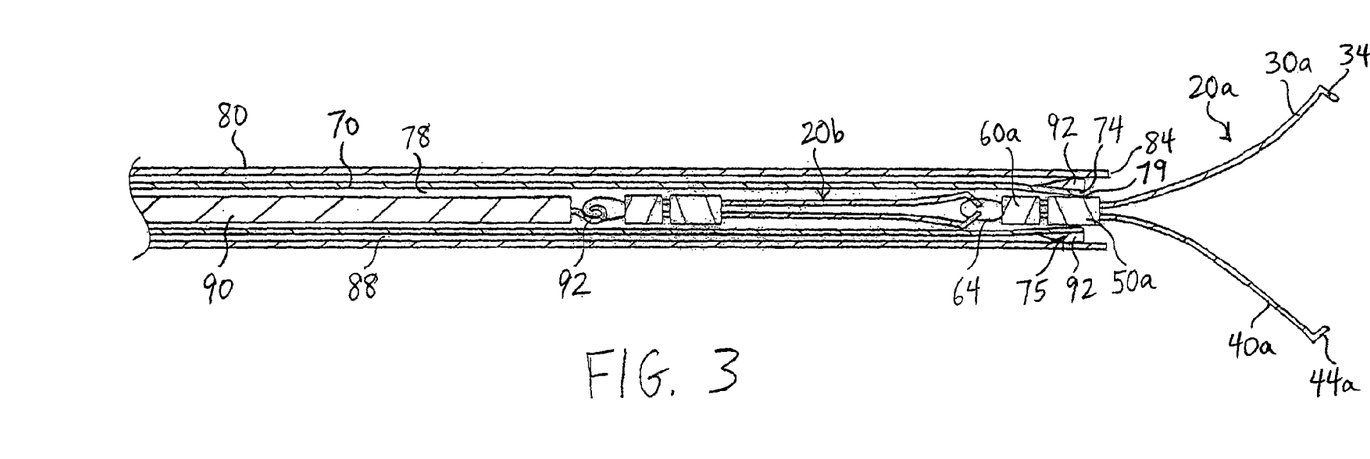

In the open state, the distal ends 34a and 44a of the first and second arms 30a and 40a, respectively, tend to be spaced apart from one another, as shown in FIGS. 2-3. The first and second arms 30a and 40a are biased to assume the open state when the distal ends 34a and 44a are no longer constrained by the inner catheter 70. The distal ends 34a and 44a may be biased to assume the open state either due to the inherent resilient properties of the material forming the first and second arms 30a and 40a, or alternatively, the first and second arms 30a and 40a may be heat-set to assume the deployed configuration shown. The first and second arms 30a and 40a may be made from any suitable resilient material such as stainless steel, nitinol, plastic, and the like. Optionally, the arms of the clip may be formed of a resorbable material such as the magnesium alloy WE43, which can dissolve over time instead of needing to pass through a patient's gastrointestinal system. Further, the first and second arms 30a and 40a may have a cross-sectional shape that is round, square, rectangular, triangular, pie-shaped, truncated cone, and the like.

Figure 4:
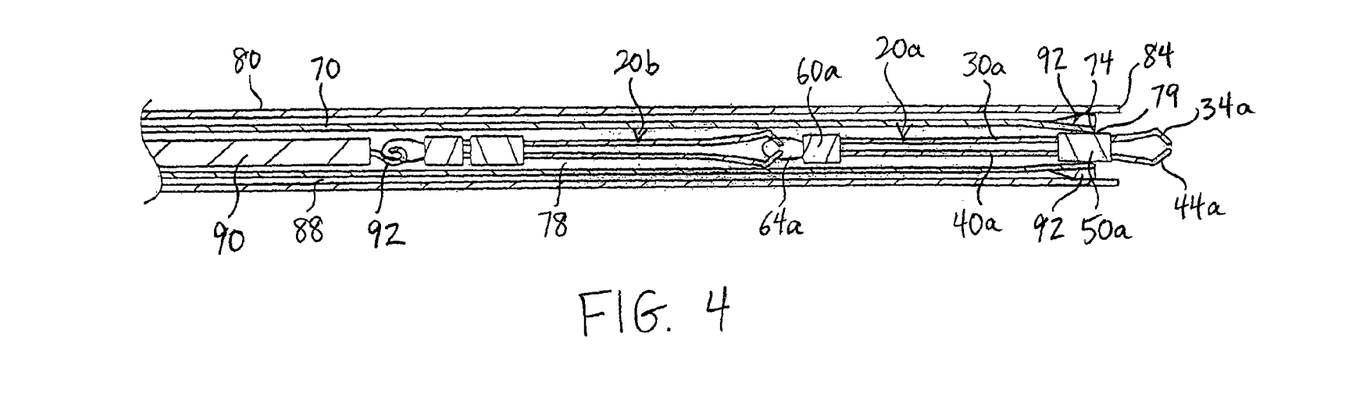
Figure 5:
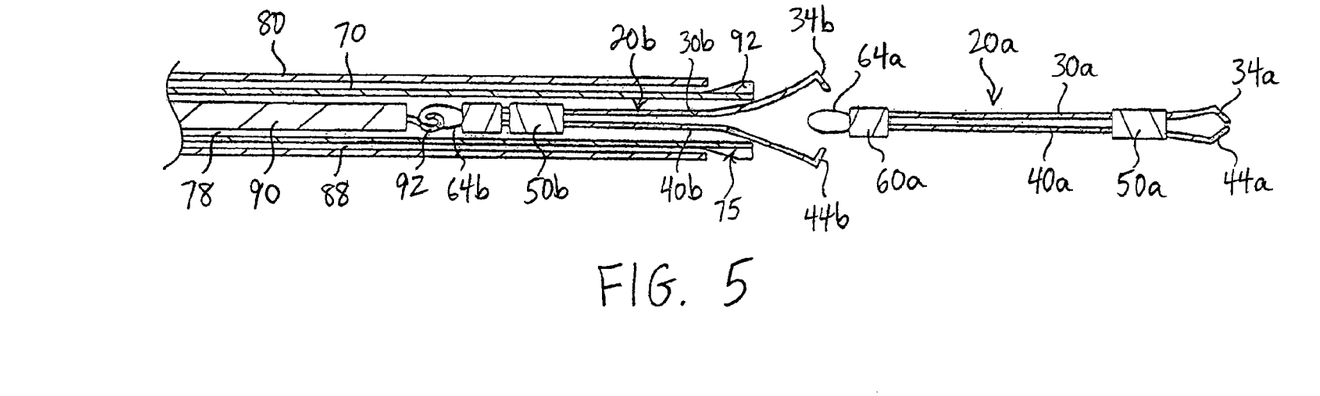

In the closed state, the sliding ring 50a is translated distally relative to the first and second arms 30a and 40a, as depicted in FIGS. 4-5 and explained further below. At this time, the distal ends 34a and 44a of the first and second arms 30a and 40a, respectively, are closed together and the tips 38a and 48a are configured to grasp tissue and facilitate tissue closure and hemostasis. The sliding ring 50a may lockingly engage the distal ends 34a and 44a of the first and second arms 30a and 40a, respectively, and may be sized so that it will not slide distally over the ends of the first and second arms 30a and 40a in the closed state. Optionally, one or more distal stop members, such as a solder or a mechanical member, may be disposed on the first arm 30a and/or the second arm 40a to limit distal advancement of the sliding ring 50a.

Referring still to FIGS. 1-5, an exemplary system is described for delivery and deployment of at least one of the clip devices. The delivery system comprises the inner catheter 70 having the lumen 78, as noted above, and further comprises an outer catheter 80 having a lumen 88. In the embodiment of FIGS. 1-5, first and second clip devices 20a and 20b are provided for sequential deployment, and the second clip device 20b is generally identical to the first clip device 20a.

The inner catheter 70 comprises an outer diameter that is less than an inner diameter of the outer catheter 80, thereby allowing the inner catheter 70 to be longitudinally advanced within the lumen 88 of the outer catheter 80. The inner catheter 70 further comprises an inner diameter that allows the first and second clip devices 20a and 20b to be loaded within the lumen 78 of the inner catheter 70, as shown in FIG. 1.

Figure 6:
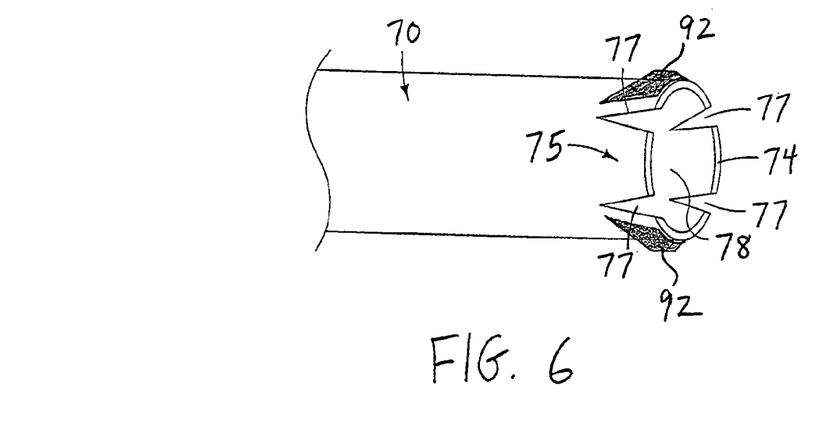
FIG. 6 is a perspective view illustrating features of a distal region of an inner catheter of the delivery system of FIGS. 1-5.

The inner catheter 70 comprises a distal end 74 and a flexible distal region 75. The flexible distal region 75 may be selectively moved in a radially inward direction, for purposes described further below. Preferably, a plurality of slits 77 are formed in the distal end 74, as shown in FIG. 6, to permit the radial flexibility along the distal region 75.

At least one wedge member 92 may be positioned along the flexible distal region 75 of the inner catheter 70. In the embodiment shown, a plurality of wedge members 92 having a tapered shape are disposed between the inner catheter 70 and the outer catheter 80, causing the flexible distal region 75 of the inner catheter 70 to move radially inward to form a constriction 79 when the outer catheter 80 is advanced against the wedge member 92, as shown in FIGS. 3-4. The wedge member 92 may comprise a biocompatible glue, plastic, metal or other suitable material, and may comprise other shapes besides the tapered shape depicted to accomplish the objectives described below. Alternatively, one or more wedge members 92 may be formed as an integral portion of the inner catheter 70 along the distal region 75.

The outer catheter 80 may comprise a rigid or substantially rigid material, such as stainless steel or plastic materials, which substantially prohibits radial outward movement of the wedge member 92 and the flexible distal region 75 of the inner catheter 70 when a distal end 84 of the outer catheter 80 covers these regions, as shown in FIGS. 3-4. However, when the distal end 84 of the outer catheter 80 is retracted proximally beyond the wedge member 92 and the flexible distal region 75 of the inner catheter 70, the flexible distal region 75 may move radially outward and the constriction 79 may be removed, as depicted in FIG. 5 below.

In one exemplary method, the first and second clip devices 20a and 20b are loaded sequentially such that the first clip device 20a is loaded distal to the second clip device 20b within the lumen 78 of the inner catheter 70, as shown in FIG.

1. A stylet 90 may be positioned in the lumen 78 at a location proximal to the second clip device 20*b*.

In one embodiment, the first and second clip devices 20*a* and 20*b* each comprise proximal retainers 64*a* and 64*b*, respectively. The proximal retainers 64*a* and 64*b* may be in the form of loop members having outer diameters that are smaller than the inner diameter of the inner catheter 70. In use, the first and second clip devices 20*a* and 20*b* may be loaded within the inner catheter 70 such that the distal ends 34*b* and 44*b* of the second clip device 20*b* securely engage the proximal retainer 64*a* of the first clip device 20*a* when the inner catheter 70 is positioned over the connection as shown in FIGS. 1-4. When the inner catheter 70 is no longer positioned over this connection, as shown in FIG. 5, the first and second clip devices 20*a* and 20*b* may disengage from one another, as explained below.

The stylet 90 may comprise a retainer 92, such as a hook member, that engages the proximal retainer 64*b* at the proximal end of the second clip device 20*b* when the inner catheter 70 is positioned over this connection, as shown in FIGS. 1-5. Accordingly, proximal and distal advancement of the stylet 90 causes a corresponding movement of the first and second clip devices 20*a* and 20*b*.

It should be noted that while two clip devices are shown in this example, any number may be used and sequentially loaded into the inner catheter 70 in an abutting manner distal to the stylet 90. Moreover, while one exemplary retainer arrangement is shown in the form of a hook and loop connection, various other retainer arrangements are possible. By way of example, alternative retainer arrangements to couple the stylet 90 to the second clip device 20*b*, and/or to couple the first and second clip devices 20*a* and 20*b* together, are described in U.S. Pat. Pub. No. 2007/0282355, the disclosure of which is hereby incorporated by reference in its entirety.

The stylet 90, the first clip device 20*a* and the second clip device 20*b* are loaded into the inner catheter 70 as shown in FIG. 1. Optionally, at this time, the outer catheter 80 may be positioned over the inner catheter 70, as shown in FIG. 3, such that the constriction 79 is formed via the wedge member 92. The constriction 79 may prevent the first and second arms 30*a* and 40*a* of the first clip device from extending distal to the inner catheter 70 to reduce the likelihood of inadvertent piercing during delivery.

Referring to FIG. 2, the outer catheter 80 is positioned proximally relative to the inner catheter 70, thereby exposing the distal region 75 of the inner catheter 70. The stylet 90 is advanced distally, relative to the inner catheter 70 and the outer catheter 80, to cause distal advancement of the second clip device 20*b* and corresponding distal advancement of the first clip device 20*a* in an abutting manner. The stylet 90 is advanced distally until the sliding ring 50*a* of the first clip device 20*a* is aligned with the distal region 75 of the inner catheter 70, as shown in FIG. 2. At this time, the distal ends 34*a* and 44*a* of the first and second arms 30*a* and 40*a*, respectively, of the first clip device 20*a* are advanced distally beyond the distal end 74 of the catheter 70, and when unconstrained, tend to bow in a radially outward direction spaced apart from one another, as depicted in FIG. 2.

Referring to FIG. 3, in a next step, the outer catheter 80 is advanced distally relative to the inner catheter 70, thereby engaging the wedge members 92 and urging the distal end 74 of the inner catheter 70 into engagement with the sliding ring 50*a*. A friction fit is achieved such that the sliding ring 50*a* is held steady. At this time, the stylet 90 may be proximally and distally advanced, thus causing corresponding movement of the first and second arms 30*a* and 40*a* relative to the sliding ring 50*a*. Thus, the sliding ring 50*a* is held steady while the first and second arms 30*a* and 40 disposed therein are advanced or retracted as desired.

In accordance with one aspect, a physician need not deploy the first clip device 20*a* at this time. Rather, the first clip device 20*a* may be moved between the open state of FIG. 3, and a state that is at least partially closed, any number of times before final deployment. For example, a physician may at least partially close the first clip device 20*a* by proximally retracting the stylet 90, and therefore the first and second arms 30*a* and 40*a*, relative to the sliding ring 50*a*, thus forcing the distal ends 34*a* and 44*a* closer together. However, before the distal ends 34*a* and 44*a* are locked closed within the sliding ring 50*a*, the physician may distally advance the stylet 90, thus distally advancing the first and second arms 30*a* and 40*a* relative to the sliding ring 50*a* and re-opening the first clip device 20*a*, e.g., for alternative positioning or grasping. Advantageously, in this manner, the first clip device 20*a* may move between the open and closed states any number of times before final deployment.

Referring now to FIG. 4, if a physician wishes to securely close the first clip device 20*a* with tissue therein, the stylet 90 and the first clip device 20*a* are retracted tightly relative to the inner catheter 70 that is holding the sliding ring 50*a*. Alternatively, the inner catheter 70 and outer catheter 80 may be advanced distally in tandem, while the stylet 90 is held steady. The result in either case is that the sliding ring 50*a* is translated distally relative to the first and second arms 30*a* and 40*a* with enough force, as shown in FIG. 4, thereby securely closing the first clip device 20*a*.

Referring now to FIG. 5, in a next step, the outer catheter 80 is proximally retracted with respect to the inner catheter 70, such that the distal end 84 of the outer catheter 80 is positioned proximal to the wedge member 92. At this time, the wedge member 92 is no longer radially constrained and the flexible distal region 75 of the inner catheter 70 may move radially outward to remove the constriction 79, as depicted in FIG. 5. The sliding ring 50*a* is no longer engaged in a friction fit with the inner catheter 70.

The stylet 90 is then advanced distally relative to the inner catheter 70 to cause the distal ends 34*b* and 44*b* of the first and second arms 30*b* and 40*b*, respectively, of the second clip device 20*b* to extend distal to the inner catheter 70. At this time, the connection between the first and second arms 30*b* and 40*b* of the second clip device 20*b* and the proximal retainer 64*a* of the first clip device 20*a* is exposed, thereby allowing the first and second clip devices 20*a* and 20*b* to detach from engagement with one another, as shown in FIG. 5.

After deployment of the first clip device 20*a*, but before deployment of the second clip device 20*b*, the sliding ring 50*b* of the second clip device 20*b* may be aligned with the distal region 75 of the inner catheter 70, in the manner explained in FIG. 2 above for the first clip device 20*a*. The sequence of deployment described in FIGS. 2-5 then may be carried out for the second clip device 20*b*. Advantageously, in this manner, any number of clip devices may be sequentially loaded into the lumen 78 of the inner catheter 70 and deployed, one at a time, without the need to remove the inner and outer catheters 70 and 80 from the patient's body and individually re-load clip devices, thereby saving operating time.

Referring to FIG. 6, and as noted above, the flexible distal region 75 of the inner catheter 70 may be selectively moved in a radially inward direction by providing a plurality of slits 77 formed in the flexible distal region 75. In the embodiment shown, four slits 77 are formed in the distal end 74 of the catheter 70 and extend in tapered manner in a distal to proximal direction. The four slits 77 may be radially spaced apart around the circumference of the catheter 70. The one or more wedge members 92 may be attached to the flexible distal region 75 at one or more locations between the slits 77. While four illustrative tapered slits 77 are shown in FIG. 6, it will be appreciated that greater or fewer slits may be employed, and they may comprise different shapes and configurations than depicted.

Figures 7, 8:
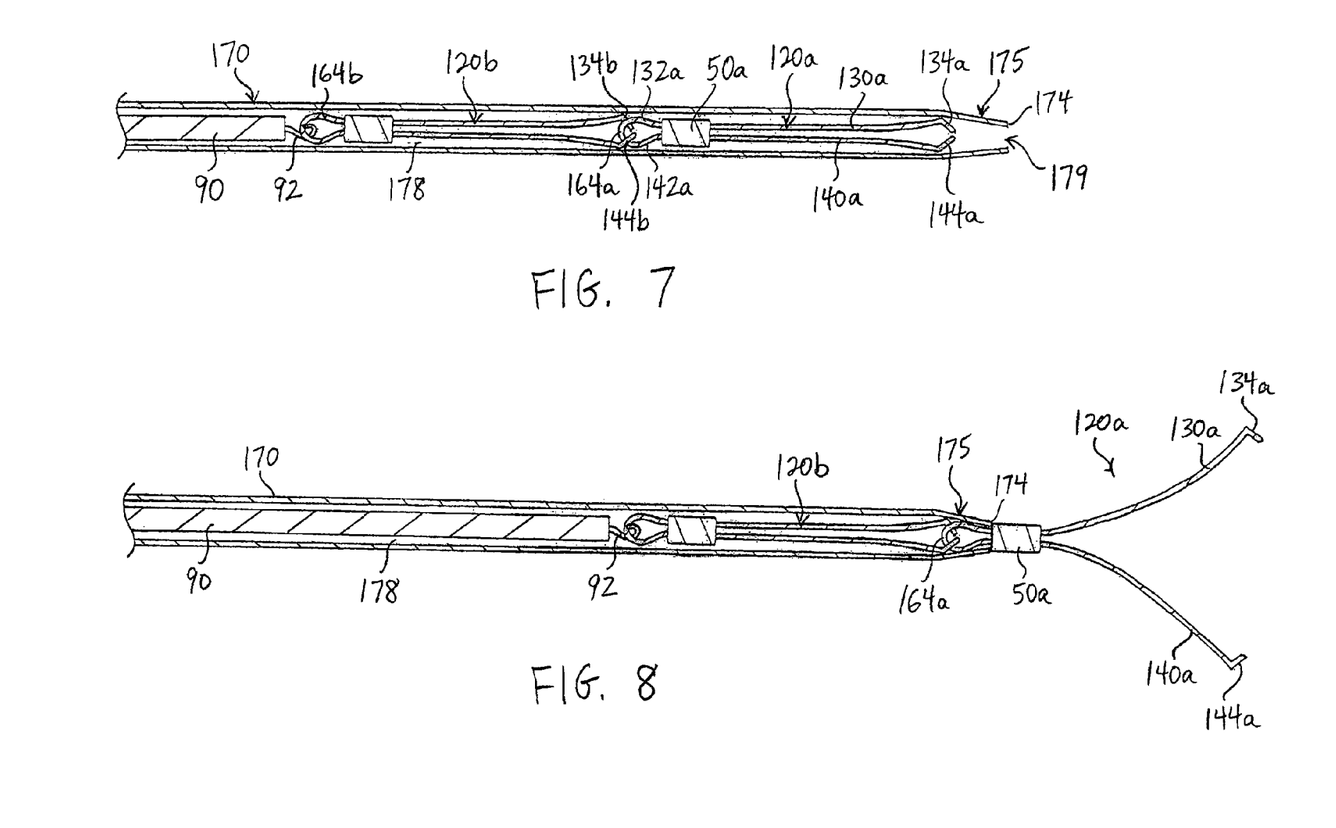
FIGS. 7-9 are side-sectional views illustrating an alternative delivery system and sequence of deployment for at least one clip device.

Referring now to FIGS. 7-10, an alternative delivery system and sequence of deployment for at least one clip device is shown. In FIGS. 7-10, an alternative first clip device 120a is similar to the first clip device 20a described above, with a main exception that proximal ends 132a and 142a of first and second arms 130a and 140a, respectively, are integrally formed into a proximal retainer 164a in the shape of a loop member, and therefore the proximal securement member 60a of FIGS. 1-5 is omitted. In this manner, the first clip device 120a may be formed from one continuous wire that is looped around at its proximal end, and where the continuous wire is bent to form distal ends 134a and 144a, as shown in FIG. 7 and described further in FIG. 12 below.

The proximal retainer 164a in the shape of the loop member has an outer diameter that is larger than the inner diameter of the sliding ring 50a, thereby limiting proximal movement of the sliding ring 50a. As in the embodiment of FIGS. 1-5, the sliding ring 50a is otherwise dimensioned to slide over the first and second arms 130a and 140a, toward the distal ends 134a and 134b of the first and second arms 130a and 140a, respectively, causing the arms to move to a closed position. The first clip device 120a has a delivery state, an open state, and a closed state, similar to the first clip device 20a described above.

The alternative delivery system of FIGS. 7-10 comprises a catheter 170 having a lumen 178, and has an inner diameter that is generally larger than an outer diameter of the first and second clip devices 20a and 20b in the delivery state, thereby allowing the first and second clip devices 20a and 20b to be loaded within the lumen 78 of the catheter 70 as shown in FIG. 1. Notably, in this embodiment, an outer catheter is omitted.

The catheter 170 comprises a distal end 174 and a tapered distal region 175. Preferably, at least one slit 177 is formed in the tapered distal region 175, as shown in FIG. 10, to permit the radial flexibility along the distal region 175.

In one exemplary method, the first and second clip devices 120a and 120b may be loaded sequentially such that the first clip device 120a is loaded distal to the second clip device 120b within the lumen 178 of the catheter 170, as shown in FIG. 7. The stylet 90 may be positioned in the lumen 178 at a location proximal to the second clip device 120b. In use, the first and second clip devices 120a and 120b may be loaded within the catheter 170 such that the distal ends 134b and 144b of the second clip device 120b securely engage the proximal retainer 164a of the first clip device 120a. Further, the retainer 92 of the stylet 90 engages the proximal retainer 164b at the proximal end of the second clip device 120b, as shown in FIG. 7. Accordingly, proximal and distal advancement of the stylet 90 causes a corresponding movement of the first and second clip devices 120a and 120b.

Figure 10:
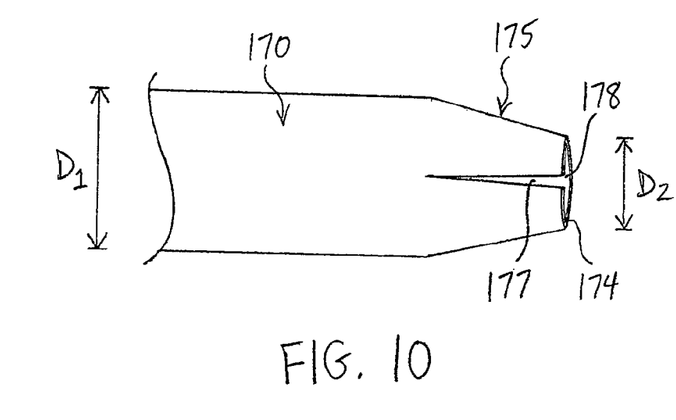
FIG. 10 is a perspective view illustrating features of a distal region of a catheter of the delivery system of FIGS. 7-9.

Notably, the catheter 170 has a first inner diameter $D_1$ at a location proximal to the tapered distal region 175, and has a smaller second inner diameter $D_2$ at the distal end 174, as shown in FIG. 10, such that the taper reduces the inner diameter from $D_1$ to $D_2$. The sliding ring 50a has an outer diameter having a size dimension between the first and second inner diameters $D_1$ to $D_2$ of the catheter 170. In the delivery state shown in FIG. 7, absent significant forces imposed thereon, the tapered distal region 175 serves to retain the first clip device 120a inside of the catheter 170 and prevents inadvertent piercing by the arms 130a and 140a.

Referring to FIG. 8, in a next step, the stylet 90 is advanced distally, relative to the catheter 170, to cause distal advancement of the second clip device 120b and corresponding distal advancement of the first clip device 120a in an abutting manner. The stylet 90 is advanced distally until the sliding ring 50a of the first clip device 120a abuts the tapered distal region 175 and is ultimately advanced distal to the tapered distal region 175 with a sufficient force. The slit 177 of the tapered distal region 175 allows the distal end 174 of the catheter 170 to flex upon application of the sufficient force imposed by the sliding ring 50a, and further, the tapered distal region 175 may be formed of a material, such as molded plastic, that facilitates such flexing upon application of the sufficient force by the sliding ring 50a. At this time, the distal ends 134a and 144a of the arms 130a and 140a, respectively, of the first clip device 120a are advanced distally beyond the distal end 174 of the catheter 170, and when unconstrained, tend to bow in a radially outward direction spaced apart from one another, as depicted in FIG. 8.

While the sliding ring 50a is disposed just distal to the tapered distal region 175 of the catheter 170, the proximal retainer 164a of the first clip device 120a is retained within the lumen 178 of the catheter 170, as shown in FIG. 8. The tapered distal region 175 of the catheter 170 may be biased such that it tends to close around the proximal retainer 164a of the first clip device 120a. At this time, the distal end 174 of the catheter 170 abuts a proximal edge of the sliding ring 50a, as depicted in FIG. 8. Since the second inner diameters $D_2$ of the catheter 70 is less than an outer diameter of the sliding ring 50a, the sliding ring 50a is prevented from being pulled back into the lumen 178 of the catheter 170.

The stylet 90 may be proximally retracted to at least partially close the first clip device 120a. However, before the distal ends 134a and 144a are locked closed within the sliding ring 50a, the physician may proximally or distally advance the stylet 90 gently, thus partially closing and re-opening the first and second arms 130a and 140a.

Figure 9:
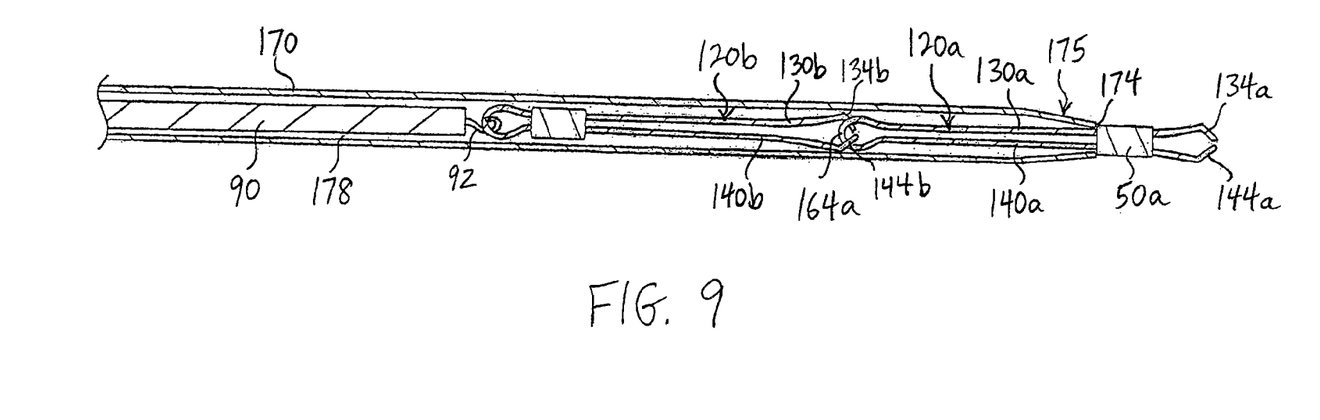

Referring to FIG. 9, if a physician wishes to securely close the first clip device 120a with tissue therein, the stylet 90 and the first clip device 120a are retracted tightly relative to the catheter 170. Alternatively, the catheter 170 may be advanced while the stylet 90 is held steady. The result in either case is that the sliding ring 50a is translated distally relative to the first and second arms 130a and 140a, as shown in FIG. 9, thereby securely closing the first clip device 120a.

Subsequently, the stylet 90 is then advanced distally relative to the catheter 170 to cause the distal ends 134b and 144b of the arms 130b and 140b, respectively, of the second clip device 120b to extend distal to the catheter 170. At this time, the connection between the first and second arms 130b and 140b of the second clip device 120b and the proximal retainer 164a of the first clip device 120a is exposed, thereby allowing the first and second clip devices 120a and 120b to detach from engagement with one another in a manner similar to the embodiment of FIG. 5.

The sequence of deployment described in FIGS. 7-9 then may be carried out for the second clip device 120b. Advantageously, in this manner, any number of clip devices may be sequentially loaded into the lumen 178 of the catheter 170 and deployed, one at a time, without the need to remove the catheter 170 from the patient's body and individually re-load clip devices, thereby saving operating time.

Figure 11:
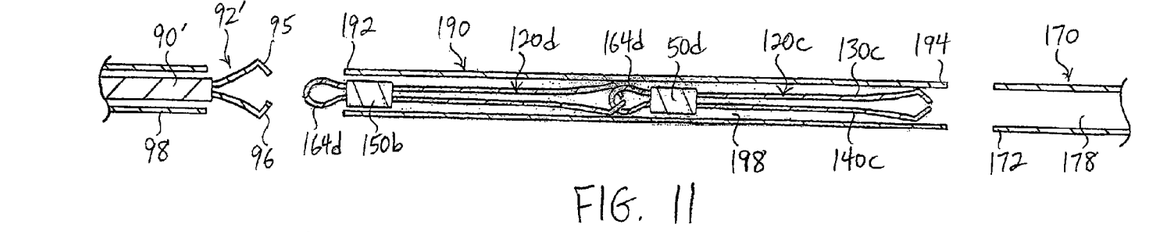
FIG. 11 is a side-sectional view of a loading cylinder that may be used in conjunction with clip delivery systems.

Referring now to FIG. 11, a loading cylinder 190 may be used in conjunction with either the embodiment of FIGS. 1-6 or FIGS. 7-10 to facilitate fast and efficient loading or reloading of one or more clip devices. In the embodiment of FIG. 11, the loading cylinder 190 comprises proximal and distal ends 192 and 194, respectively, and a lumen 198 extending therebetween. The loading cylinder 190 may comprises inner and outer diameters that are identical to inner and outer diameters of the inner catheter 70 of FIGS. 1-6 or the catheter 170 of FIGS. 7-10. Optionally, an engagement mechanism (not shown) may be provided to selectively couple the distal end 194 of the loading cylinder 190 with the proximal end 172 of the catheter 170, to thereby ensure a correct alignment between the lumen 198 of the loading cylinder 190 and the lumen 178 of the catheter 170.

In the example of FIG. 11, two additional clip devices 120c and 120d, which are identical to the clip devices 120a and 120b of FIGS. 7-9, are loaded into the lumen 198 of the loading cylinder 190 as shown. The proximal retainer 164d of the clip device 120d may extend just outside of the proximal end 192 of the loading cylinder 190, as shown in FIG. 11, for subsequent engagement with a retainer 92' of an alternative stylet 90'. The alternative stylet 90' is similar to the stylet 90 described above, with an exception that the retainer 92'comprises arms 95 and 96, which are similar in structure to the distal ends 134a and 144a of the first clip device 120a.

In use, a physician may deploy the clip devices 120a and 120b in the manner described in FIGS. 7-9 above. The loading cylinder 190, carrying additional clip devices 120c and 120d, may be provided in the operating room. If the additional clip devices 120c and 120d are needed, the stylet 90' is retracted from within the lumen 178 of the catheter 170, and may be withdrawn towards a sheath 98 as depicted in FIG. 11. The distal end 194 of the loading cylinder 190 then is aligned with the proximal end 172 of the catheter 170, such that the lumen 198 of the loading cylinder 190 is aligned with the lumen 178 of the catheter 170. The arms 95 and 96 of the retainer 92' of the stylet 90' then are joined to the proximal retainer 164d of the clip device 120d and urged distally into the loading cylinder 190. Distal advancement of the stylet 90' causes corresponding distal advancement of the clip devices 120c and 120d through the lumen 178 of the catheter 170, and the deployment of the clip devices 120c and 120d may be carried out in the manner described above. Advantageously, the endoscope and catheters can remain in place within the body of the patient, retaining access to the bleeding site, and facilitating a faster procedure. The catheters 70 and 170 described above can be reloaded as many times as needed using one or more loading cylinders 190. Moreover, different loading cylinders 190 can be provided with different clip styles.

Figure 12:
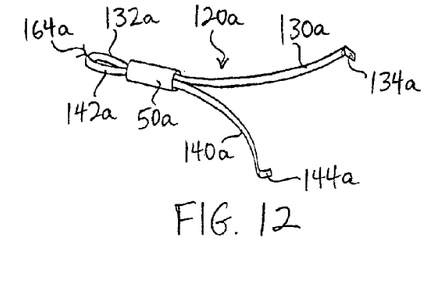
FIG. 12 is a perspective view of the clip device of FIGS. 7-9.

Referring now to FIGS. 12-15, features of various possible clip designs are shown. In FIG. 12, the clip device 120a of the embodiment of FIGS. 7-10 is shown in isolation. In one embodiment, the clip device 120a has a length in the delivery state of between about 10 mm to about 25 mm. In the open state, the distance between the distal ends 134a and 144a of the first and second arms 130a and 140a, respectively, may be between about 6 mm to about 10 mm. The wire forming the clip device 120a may comprise a flat wire having a width of about 0.8 mm to about 1.0 mm, and a thickness of about 0.1 mm to about 0.2 mm. When used in conjunction with a delivery system as shown in FIGS. 1-6 or FIGS. 7-10, the clip device 120a and associated sliding ring 50a can fit down an endoscope channel having a 2.8 mm or 3.2 mm diameter. As noted above, the clip device 120a can be formed of any suitable material such as nitinol or another material that may be biased to assume the open state shown in FIG. 12 upon removal from a delivery catheter, and optionally may be formed of a resorbable material.

Figure 13:
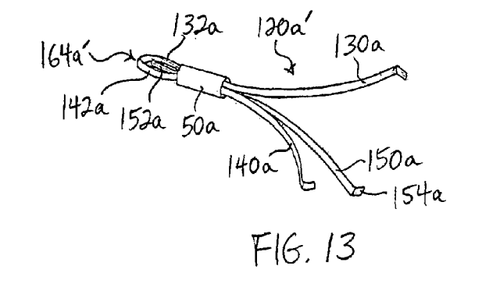
FIG. 13 is a perspective view of an alternative clip device.

In FIG. 13, an alternative clip device 120a' is formed from a wire that is bent to form the first and second arms 130a and 140a, as explained in FIGS. 7-9 and FIG. 12 above, however an additional wire segment is provided and forms a third arm 150a having a proximal end 152a and a distal end 154a. A three-prong clip device 120a' therefore is provided. The proximal end 152a of the third arm 150a may be soldered to a portion of the loop formed by the proximal ends 132a and 142a of the arms 130a and 140a, respectively, thereby forming a proximal retainer 164a. In a further alternative, a clip device may be similar to the clip device 120a', but may comprise a fourth arm, whereby the four arms may be equally spaced apart about 90 degrees from one another, or variably spaced apart at other distances from one another.

Figure 14:
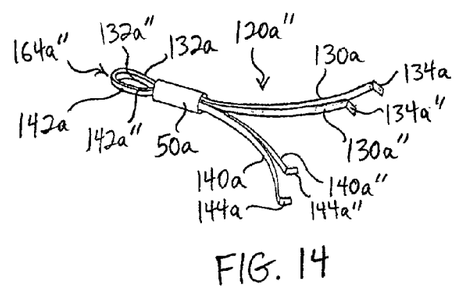
FIG. 14 is a perspective view of a further alternative clip device.

In FIG. 14, an alternative clip device 120a" is substantially identical to the clip device 120a, with the exception that an additional wire is disposed inward of the wire forming the first and second arms 130a and 140a. The additional wire forms third and fourth arms 130a" and 140a" having proximal ends 132a" and 142a", respectively. The proximal ends 132a" and 142a" form a loop member disposed inside of the loop member formed by the proximal ends 132a and 142a of the first and second arms 130a and 140a, respectively, as shown in FIG. 14, to form a proximal retainer 164a". Further, the third and fourth arms 130a" and 140a" have distal ends 134a" and 144a", which may be slightly offset from the distal ends 134a and 144a of the first and second arms 130a and 140a, respectively, as shown in FIG. 14.

Figure 15:
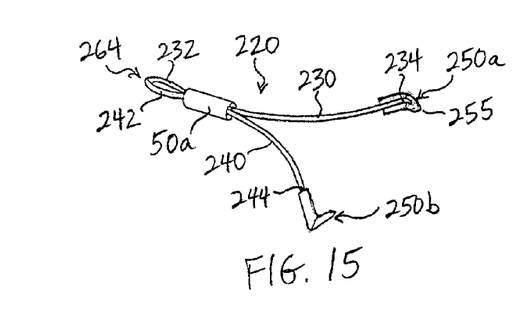
FIG. 15 is a perspective view of yet a further alternative clip device.

In FIG. 15, an alternative clip device 220 is similar to the clip device 120a in that one wire is bent to form first and second arms 230 and 240 having proximal ends 232 and 234, respectively, which are coupled together to form a proximal retainer 264 in the shape of a loop member. The first and second arms 230 and 240 further comprise distal ends 234 and 244, respectively. In this embodiment, the wire forming the first and second arms comprises a round cross-sectional shape. In order to provide a larger and sharper surface area to engage tissue, grasping members 250a and 250b are coupled to exterior surfaces of the distal ends 234 and 244 of the first and second arms 230 and 240, respectively. The grasping members 250a and 250b may be coupled to the first and second arms 230 and 240 using a solder, weld, mechanical connection, or other suitable technique. Preferably, the grasping members 250a and 250b comprise sharpened distal tips 255 that are bent radially inward to securely engage tissue. It will be appreciated that where flat wire cross-sections are depicted herein, round wire cross-sections may be provided, and vice versa.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A system for deploying at least one clip device, the system comprising:
  a first clip device having first and second arms, wherein distal ends of the first and second arms tend to be spaced apart from each other when the first clip device is in an open state, and wherein the distal ends of the first and second arms are adjacent to each other when the first clip device is in a closed state;

a sliding ring being movable between a first position when the first clip device is in the open state and a second position to hold the first and second arms of the first clip device in the closed state;

an inner catheter having a lumen, wherein the first clip device and the sliding ring are configured to be selectively advanced through the lumen of the inner catheter; and an outer catheter having a lumen, wherein the inner catheter is configured for longitudinal movement with respect to the lumen of the outer catheter, wherein selective positioning of the outer catheter over a distal region of the inner catheter causes the distal region of the inner catheter to bow radially inward to form a constriction that selectively engages the sliding ring of the first clip device using a friction fit, so that the sliding ring does not move either proximally or distally.

2. The system of claim 1, wherein the first and second arms of the first clip device are movable longitudinally relative to the sliding ring while the sliding ring is engaged by the constriction of the inner catheter, to permit selective movement of the first and second arms between the open state and a partially closed state.

3. The system of claim 1, further comprising at least one wedge member disposed at the distal region of the inner catheter, wherein the outer catheter is configured to selectively engage the wedge member to form the constriction when the outer catheter is positioned over the distal region of the inner catheter.

4. The system of claim 3, wherein the distal region of the inner catheter comprises at least one slit formed in a distal end of the inner catheter, wherein the at least one slit facilitates movement of the distal region of the catheter in a radially inward direction.

5. The system of claim 1, wherein multiple clip devices are configured to be loaded in a sequential manner within the lumen of the inner catheter at the same time, and further are configured to be individually and selectively deployed from a distal end of the inner catheter.

6. The system of claim 5 further comprising:
a second clip device having first and second arms, wherein distal ends of the first and second arms tend to be spaced apart from each other when the second clip device is in an open state, and wherein the distal ends of the first and second arms are adjacent to each other when the second clip device is in a closed state; and a stylet disposed for longitudinal movement within the lumen of the inner catheter, wherein the second clip device is configured to be disposed within the lumen of the inner catheter at a location distal to the stylet during delivery, and wherein the first clip device is configured to be disposed in the lumen of the inner catheter at a location distal to the second clip device during delivery, wherein distal advancement of the stylet is adapted to cause distal advancement of the first and second clip devices to selectively deploy the first clip device and, subsequently, selectively deploy the second clip device.

7. The system of claim 6 wherein the first clip device comprises a proximal retainer adapted to securely engage the distal ends of the first and second arms of the second clip device within the lumen of the inner catheter, wherein the proximal retainer comprises a continuous loop formed by proximal ends of the first and second arms of the first clip device.

8. The system of claim 6 wherein proximal ends of the first and second arms of the first clip device are joined together by a proximal securement member, and wherein a proximal retainer is coupled to the proximal securement member and configured for engagement with the distal ends of the first and second arms of the second clip device within the lumen of the inner catheter.

9. A system for deploying at least one clip device, the system comprising:
a first clip device having first and second arms, wherein distal ends of the first and second arms are biased towards an open state in which they are spaced apart from each other, and wherein the distal ends of the first and second arms are adjacent to each other when the first clip device is in a closed state;

a sliding ring being movable between a first position when the first clip device is in the open state and a second position to hold the arms of the first clip device in the closed state; and a catheter having proximal and distal ends, a lumen extending therebetween, and a tapered distal region, wherein the catheter comprises a first inner diameter at a location proximal to the tapered distal region, and further has a second inner diameter at the distal end, wherein the second inner diameter is less than the first inner diameter, wherein the sliding ring comprises an outer diameter that is less than the first inner diameter of the catheter and greater than the second inner diameter of the catheter, wherein the tapered distal region of the catheter is integral to the catheter, is directly adjacent to the first clip device in a delivery state, and is flexible such that application of a predetermined distally-oriented force imposed by the sliding ring ejects the sliding ring from the distal end of the catheter, and wherein there is no outer catheter surrounding the tapered distal region of the catheter.

10. The system of claim 9 wherein, upon ejection of the sliding ring from the distal end of the catheter, the sliding ring is dimensioned to abut the distal end of the catheter.

11. The system of claim 10 wherein, upon ejection of the sliding ring from the distal end of the catheter, proximal retraction of the first and second arms of the first clip device relative to the sliding ring moves the first clip device between the open and closed states.

12. The system of claim 9 wherein the tapered distal region of the catheter comprises at least one slit formed in the distal end of the catheter, wherein the at least one slit facilitates movement of the tapered distal region of the catheter in a radially outward direction.

13. The system of claim 9 wherein multiple clip devices are configured to be loaded in a sequential manner within the lumen of the catheter at the same time, and further are configured to be individually and selectively deployed from the distal end of the catheter.

14. The system of claim 13 further comprising:
a second clip device having first and second arms, wherein distal ends of the first and second arms tend to be spaced apart from each other when the second clip device is in an open state, and wherein the distal ends of the first and second arms are adjacent to each other when the second clip device is in a closed state; and a stylet disposed for longitudinal movement within the lumen of the catheter, wherein the second clip device is configured to be disposed in the lumen of the catheter at a location distal to the stylet during delivery, and wherein the first clip device is configured to be disposed in the lumen of the catheter at a location distal to the second clip device during delivery, wherein distal advancement of the stylet is adapted to cause distal advancement of the first and second clip devices to selectively deploy the first clip device and, subsequently, selectively deploy the second clip device.

15. The system of claim 14, wherein the first clip device comprises a proximal retainer adapted to securely engage the distal ends of the first and second arms of the second clip device within the lumen of the catheter, wherein the proximal retainer is disposed at a location proximal to the sliding ring, and wherein the proximal retainer is configured to be retained within the lumen of the catheter when the sliding ring is ejected distal to the catheter.

16. The system of claim 15, wherein the proximal retainer comprises a continuous loop formed by proximal ends of the first and second arms of the first clip device.

17. A system for deploying at least one clip device, the system comprising:

a first clip device having first and second arms, wherein distal ends of the first and second arms tend to be spaced apart from each other when the first clip device is in an open state, and wherein the distal ends of the first and second arms are adjacent to each other when the first clip device is in a closed state;

a sliding ring being movable between a first position when the first clip device is in the open state and a second position to hold the first and second arms of the first clip device in the closed state;

an inner catheter having a lumen, wherein the first clip device and the sliding ring are configured to be selectively advanced through the lumen of the inner catheter; and an outer catheter having a lumen, wherein the inner catheter is configured for longitudinal movement with respect to the lumen of the outer catheter, wherein selective positioning of the outer catheter over a distal region of the inner catheter causes the distal region of the inner catheter to bow radially inward to form a constriction that selectively engages the sliding ring of the first clip device using a friction fit, wherein the sliding ring has first and second ends, and the constriction engages the sliding ring between the first and second ends.

18. The system of claim 17, wherein the first and second arms of the first clip device are movable longitudinally relative to the sliding ring while the sliding ring is engaged by the constriction of the inner catheter, to permit selective movement of the first and second arms between the open state and a partially closed state.

19. The system of claim 17, further comprising at least one wedge member disposed at the distal region of the inner catheter, wherein the outer catheter is configured to selectively engage the wedge member to form the constriction when the outer catheter is positioned over the distal region of the inner catheter.

20. The system of claim 19, wherein the distal region of the inner catheter comprises at least one slit formed in a distal end of the inner catheter, wherein the at least one slit facilitates movement of the distal region of the catheter in a radially inward direction.

* * * * *